(12) United States Patent
Bespalov et al.

(10) Patent No.: US 8,972,193 B2
(45) Date of Patent: Mar. 3, 2015

(54) FORMATION RESISTIVITY IMAGER WITH REDUCED LEAKAGE TO MANDREL

(75) Inventors: Alexandre N. Bespalov, Spring, TX (US); Assol Kavtorina, legal representative, Spring, TX (US); Gregory B. Itskovich, Houston, TX (US); Stanislav Wilhelm Forgang, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 457 days.

(21) Appl. No.: 13/411,814

(22) Filed: Mar. 5, 2012

(65) Prior Publication Data

US 2013/0024120 A1 Jan. 24, 2013

Related U.S. Application Data

(60) Provisional application No. 61/478,985, filed on Apr. 26, 2011.

(51) Int. Cl.
*G06F 19/00* (2011.01)
*G01N 33/24* (2006.01)
*G01V 3/20* (2006.01)

(52) U.S. Cl.
CPC . *G01N 33/24* (2013.01); *G01V 3/20* (2013.01)
USPC .............................................................. 702/7

(58) Field of Classification Search
USPC ........................... 702/7, 13, 14, 182–185, 188
See application file for complete search history.

(56) References Cited

U.S. PATENT DOCUMENTS

| | | | |
|---|---|---|---|
| 6,636,046 B2 | 10/2003 | Lee et al. | |
| 7,385,401 B2 | 6/2008 | Itskovich et al. | |
| 7,394,258 B2 | 7/2008 | Itskovich et al. | |
| 7,397,250 B2 | 7/2008 | Bespalov et al. | |
| 2005/0206385 A1 | 9/2005 | Strack et al. | |
| 2008/0128166 A1 | 6/2008 | Forgang et al. | |
| 2011/0227580 A1 | 9/2011 | Gold et al. | |
| 2012/0068711 A1* | 3/2012 | Forgang | 324/324 |

OTHER PUBLICATIONS

Notification of Transmittal of the International Search Report and the Written Opinion of the International Searching Authority, or the Declaration; PCT/US2012/034975; Dec. 3, 2012.

Hagiwara, et al. "Effects of Mandrel, Borehole, and Invasion for Tilt-Coil antennas". SPE84245, SPE Annual Technical Conference and Exhibition, Denver, Oct. 5-8, 2003. pp. 255-263.

* cited by examiner

*Primary Examiner* — Edward Raymond
(74) *Attorney, Agent, or Firm* — Cantor Colburn LLP

(57) ABSTRACT

A method of estimating a parameter of a formation contacting a borehole with an instrument that includes a mandrel and a pad includes providing a measurement voltage to the pad; applying a biasing voltage to the mandrel while the measurement voltage is applied to the pad; measuring a received current during at least a portion of time the measurement voltage is provided; and estimating the parameter based on the received current.

16 Claims, 5 Drawing Sheets

FORMATION RESISTIVITY IMAGER WITH REDUCED LEAKAGE TO MANDREL

CROSS-REFERENCE TO RELATED APPLICATIONS AND PRIORITY CLAIM

This application claims the benefit of U.S. Provisional Application Ser. No. 61/478,985, entitled "FORMATION RESISTIVITY IMAGER WITH REDUCED LEAKAGE TO MANDREL", filed Apr. 26, 2011, under 35 U.S.C. §119(e), which is incorporated herein by reference in its entirety.

BACKGROUND

1. Field of the Invention

The present invention generally relates to drilling boreholes and, particularly, to a resistivity imager.

2. Description of the Related Art

In underground drilling applications, such as oil and gas exploration and recovery, a borehole is drilled into the earth. As a part of the drilling process, drilling mud is typically introduced into the borehole. One type of drilling mud is referred to as "oil-based" mud, while another is "water-based" mud. Other fluids may be found in a borehole as well. For example, boreholes may include formation fluids such as oil, gas, water, saline water as well as various combinations of these and other fluids. The various fluids found in a borehole can present complications for imaging of the formation.

One technique for imaging downhole formations is that of resistivity imaging. Resistivity imaging can be performed while drilling or at a later time. In general, resistivity imaging includes utilizing a resistivity instrument that provides a voltage to a formation and measures a current received from the formation. Utilizing Ohm's law, the resistivity of the formation is based on the relationship between the applied voltage and the measured current.

Many factors can affect the resolution of the resistivity imaging instruments. For example, instrument standoff (i.e., the gap between the wall of the borehole and the voltage source and/or current sensor), variability of the standoff, and variability of the electrical properties of the drilling mud as well as the formation can all affect resolution of the resistivity imaging instrument.

One particular challenging situation for imaging low resistivity formations, such as in the Gulf of Mexico, arises in the wells where the oil-based mud has been used as a drilling fluid. Oil-based mud is typically characterized by a very high value of resistivity. That is, total impedance, measured by a resistivity imaging instrument, primarily includes three sequentially connected impedances formed respectively by the formation, the drilling fluid, and the instrument measurement circuit itself. Typically, impedance of the instrument measurement circuit has been known and small compared to those of the formation and drilling fluid, and, therefore, could be easy accounted for or often neglected. Accordingly, sensitivity of the instrument to the changes in resistivity of the formation deteriorates as a contribution of the formation into the overall impedance goes down.

What are needed are techniques for enhancing resistivity images taken downhole. Preferably, the techniques provide improved image quality in the conditions of oil-based mud and low resistive formations.

BRIEF SUMMARY

In one embodiment, a method of estimating a parameter of a formation contacting a borehole with an instrument that includes a mandrel and a pad is disclosed. The method of this embodiment includes: providing a measurement voltage to the pad; applying a biasing voltage to the mandrel while the measurement voltage is applied to the pad; measuring a received current during at least a portion of time the measurement voltage is provided; and estimating the parameter based on the received current.

According to another embodiment, a method of estimating a parameter of a formation contacting a borehole with an instrument that includes a mandrel and a pad is disclosed. The method of this embodiment includes: providing a measurement voltage to the pad; applying a first biasing voltage to the mandrel while the measurement voltage is applied to the pad; measuring a first total current provided to the pad while the first biasing voltage is applied; measuring a first received current while the first biasing voltage is provided; applying a second biasing voltage to the mandrel while the measurement voltage is applied to the pad and after the first biasing voltage is applied; measuring a second received current while the second biasing voltage is provided; measuring a second total current applied provided to the pad while the second biasing voltage is applied; and estimating the parameter based on the first and second received currents and the first and second total currents.

According to yet another embodiment, a measurement instrument for measuring a parameter of formation contacting a borehole is disclosed. The measurement instrument of this embodiment includes a mandrel and a pad that carries a transmitting element and a measurement electrode and that is coupled to the mandrel such that it can be extended outwardly away from the mandrel to contact the formation. The measurement instrument of this embodiment also includes a measurement voltage provider that provides a measurement voltage to the transmitting element and a biasing voltage provider that provides a biasing voltage to the mandrel at least a portion of the time the measurement voltage is provided.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method presented herein by way of exemplification and not limitation with reference to the Figures. In particular, disclosed herein is a resistivity imaging instrument that uses currents flowing between the instrument and surrounding earth formations for generation of high resolution resistivity images. Aspects of the instrument as well as techniques for processing data are provided.

Figure 1:
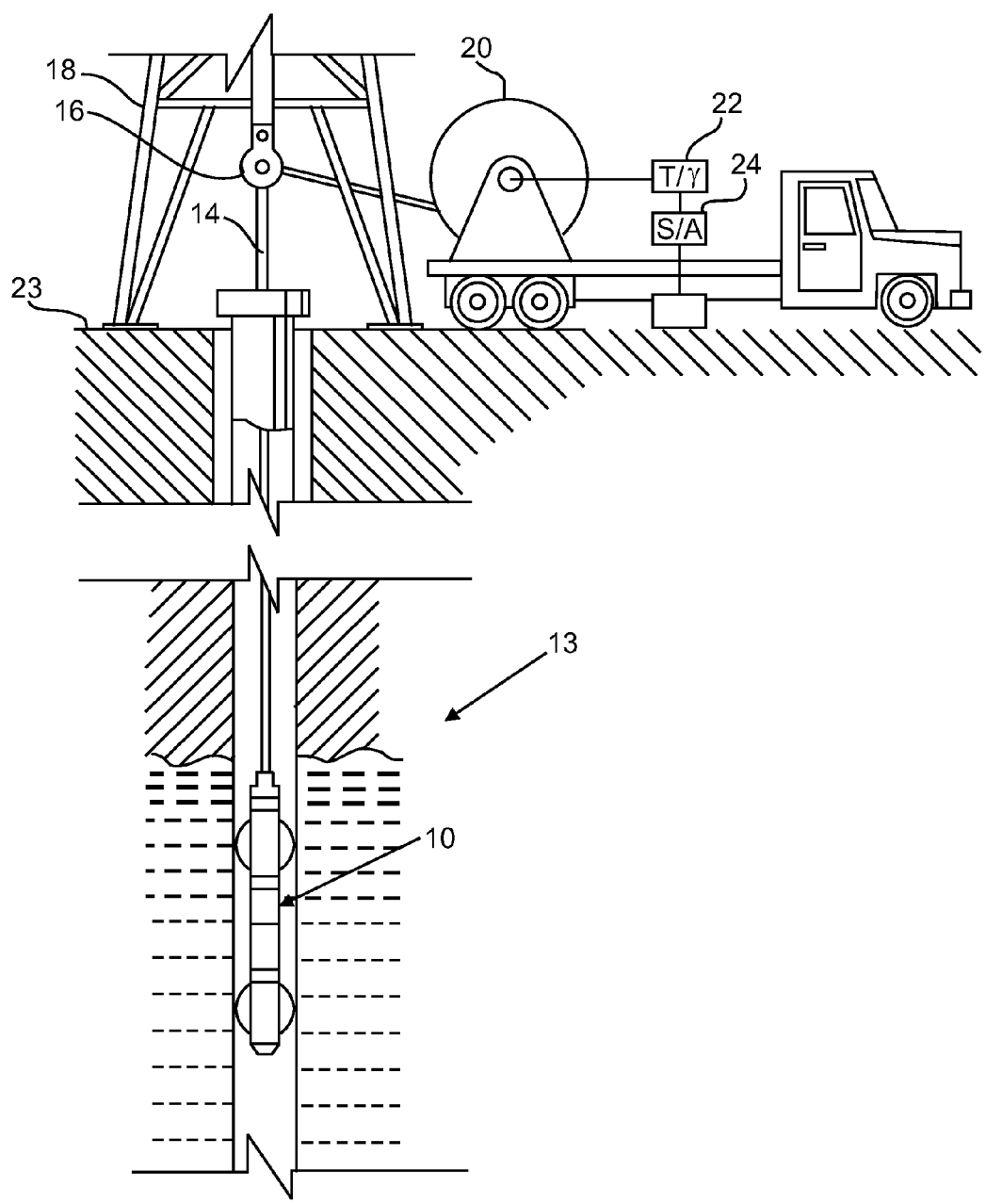
FIG. 1 illustrates an exemplary embodiment of a resistivity instrument disposed in a borehole penetrating the earth.

FIG. 1 illustrates an exemplary imaging instrument 10 suspended in a borehole 12. The imaging instrument 10 (e.g., a phase-sensitive galvanic imager) penetrates earth formations such as formation 13, from a suitable cable 14 that passes over a sheave 16 mounted on a drilling rig 18. Typically, the cable 14 includes a stress member and various conductors for transmitting commands to the instrument 10, for receiving data from the instrument 10 as well as providing power. The instrument 10 is raised and lowered by draw works 20. An electronics module 22, shown on the surface 23, transmits the required operating commands downhole and in return, receives data back. The data may be recorded on an archival storage medium of any desired type for concurrent or later processing. The data may be transmitted in analog or digital form. Data processors such as a suitable computer 24 may be provided for performing data analysis in the field in real time or the recorded data may be sent to a processing center or both for post processing of the data. It shall be understood, however, that the instrument 10 can also include one or more data processors. Accordingly, in the embodiments disclosed below, processing of receiving information can take place at either or both of the instrument or the computer 24. Furthermore, the computer 24 can be formed by a plurality of computing devices in certain instances.

Figure 2:
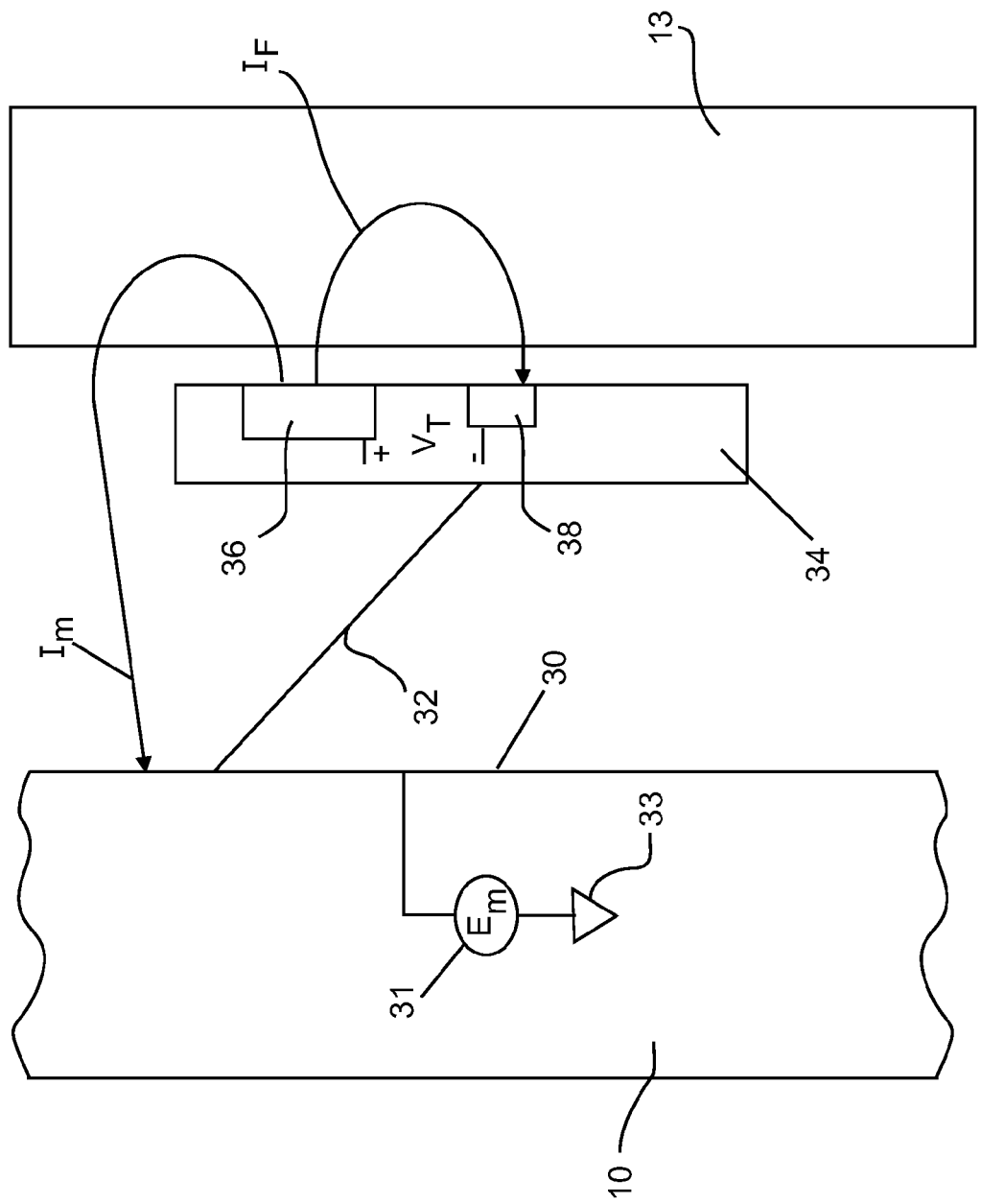
FIG. 2 illustrates a pad of the resistivity instrument in contact with a formation under examination.

FIG. 2 illustrates a portion of the exemplary imaging instrument 10 in an operating position taking resistivity measurements of formation 13. The instrument 10 includes an outer body portion commonly referred to as a mandrel 30. The mandrel 30 provides an outer surface to protect electronic or other elements of the imaging instrument 10. The mandrel 30 also supports one or more pads 34. In FIG. 2, only a single pad 34 is illustrated but it shall be understood that the mandrel 30 can support several pads 34. In the illustrated example, a support member in the form of an articulating arm 32 causes the pad to press against or otherwise contact the formation 13. Of course, the pad 34 could be formed as part of the mandrel 30 or attached directly to it. In such an embodiment, the articulating arm 32 may be omitted.

The pad 34 can be formed in many different manners as is known in the art. In one implementation, the pad 34 includes a transmitting element 36 and one or more measurement electrodes 38. The transmitting element 36 can be a metal plate in one embodiment. The transmitting element 36 can induce a current through the formation 13 when a voltage $E_0$ is provided to it. In particular, an alternating current (A.C.) transmitting voltage ($E_0$) causes a formation current $I_F$ to flow between the transmitting element 36 and the measurement electrode 38. The measurement electrode 38 is occasionally referred to as a "button" in the industry. In the illustrated embodiment, $E_0$ is measured between the transmitting element 36 and the measurement electrode 38 with the measurement electrode 38 serving as the neutral. Based on Ohm's law, the resistivity (or impedance) of the formation 13 can be generally be determined by measuring $E_0$ and the current measured by the measurement electrode 38 ($I_F$).

It has been discovered, however, that not all of the current induced by the transmitting element 36 actually travels form the transmitting pad 36 to the measurement electrode 38. Indeed, in some cases, a leakage current $I_L$ is induced from the formation to the mandrel 30. The magnitude of the leakage current $I_L$ cannot typically be measured and, as such, is an unknown quantity that can degrade the accuracy of resistivity measurements.

In FIG. 2 and in the following discussion each pad 34 is illustrated as containing a single transmitting element 36 and a single measurement electrode 38. Of course, the pad could include additional transmitting elements 36 and measurement electrodes 38.

Figure 3:
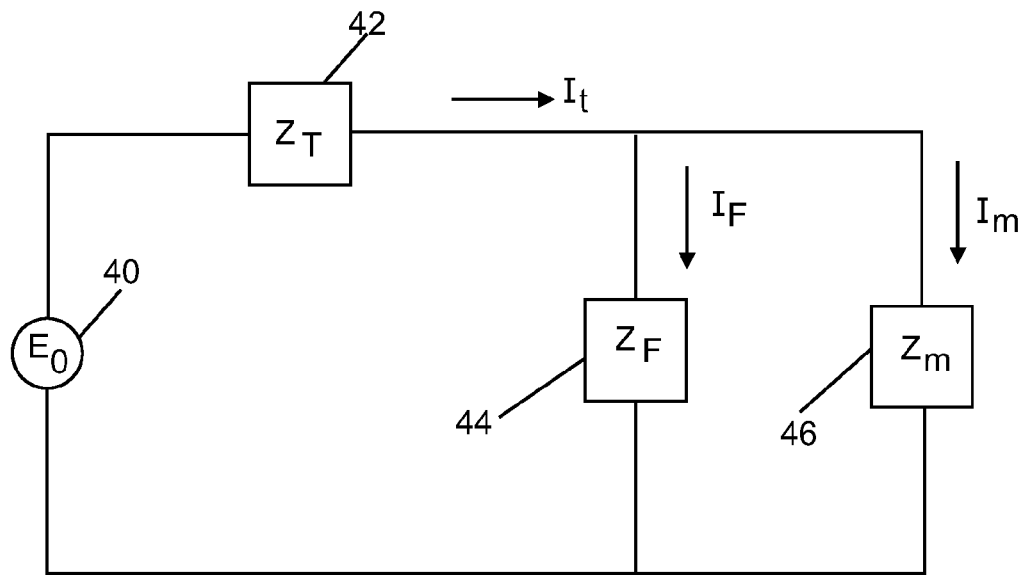
FIG. 3 illustrates a circuit diagram that models the electrical behavior of the instrument when the pad is at some standoff from the formation.

FIG. 3 shows a circuit diagram that models the electrical behavior of the instrument 10 when the pad 34 is at some standoff from the formation 13 according to one operational mode of the instrument 10. In the following discussion, it shall be assumed that any drilling mud between the pad 34 and the formation is non-conductive.

In more detail, and referring now to both FIGS. 2 and 3, the circuit shown in FIG. 3 includes a voltage source 40 that provides transmitting voltage ($E_0$) that is provided to the transmitting element 36. $E_0$ is a time varying voltage in one embodiment. The circuit also includes a transmitting impedance 42 ($Z_T$) that includes the capacitance ($C_T$) between the transmitting element 36 and the formation 13 and a resistor $R_T$ which depends on the resistivity of the formation and the size of the transmitting element 36. The current ($I_T$) created by the transmitting element 38 is split between the $I_F$ and $I_m$. The values of $I_F$ and $I_m$ depend, respectively, on the measurement electrode impedance 44 ($Z_F$) and the mandrel impedance 46 ($Z_m$).

The value of $Z_F$ depends on capacitance $C_F$ between the formation and the measurement electrode 38, a resistor $R_F$ which depends on the resistivity of the formation 13 and the size of the measurement electrode 38. The value of $Z_m$ depends on the capacitance ($C_m$) and inductance ($L_m$) between the formation 13 and the mandrel 30 as well as a resistance ($R_m$) that depends on the resistivity of the formation 13, frequency, and possibly other factors. For ease of discussion, only impedances 44 and 46 need be considered. It shall be understood, that in one embodiment, the instrument 10 may only be able to measure $E_0$ and $I_F$ and that $I_F$ can be converted into an impedance to form an impedance image as is known in the art.

Having discovered that the leakage current $I_m$ exists, embodiments of the present invention include biasing the mandrel 30 such that $I_m$ is reduced or eliminated.

Figure 4:
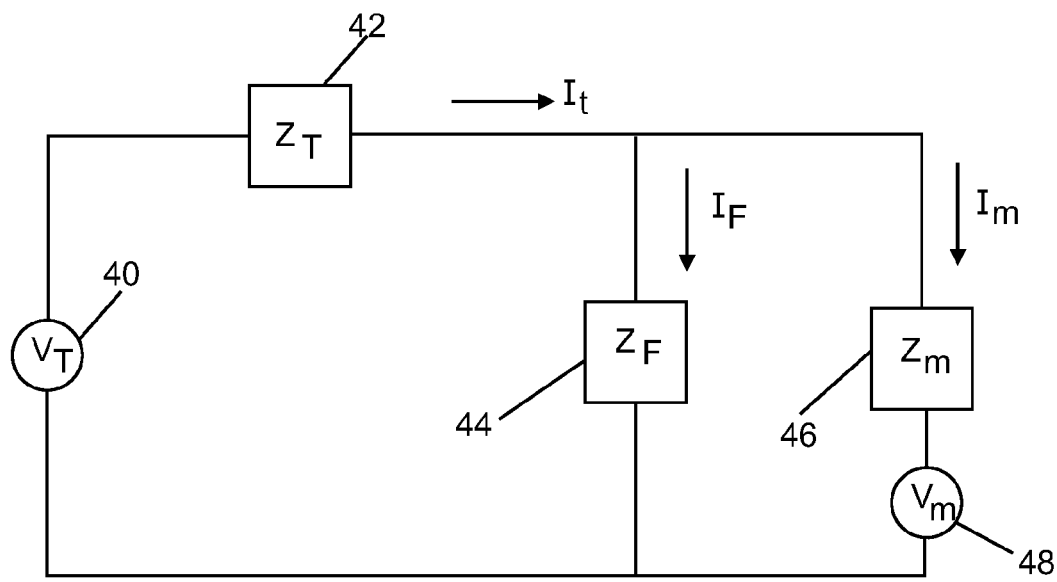
FIG. 4 illustrates a circuit diagram that models the electrical behavior of the instrument when the pad is at some standoff from formation and the mandrel of the instrument is coupled to a biasing voltage.

FIG. 4 illustrates a circuit representation of a system according to one embodiment of the present invention. The circuit in FIG. 4 is similar to the circuit shown in FIG. 3 but includes a biasing voltage $E_m$. $E_m$ represents a voltage that raises the mandrel 30 to a higher electric potential than the measurement electrode 38. As such, the measurement electrode 38 becomes a more attractive destination for current. In this manner, $I_m$ can be reduced or eliminated. Such reduction or elimination of $I_m$ can, of course, increase the accuracy of resistivity measurements made by instrument 10.

Specifically, according to one embodiment, the value of the biasing voltage $E_m$ is selected to minimize or otherwise reduce $I_m$. Based on the circuit of FIG. 4 and Kirchoff's laws, a system of three equations (1) can be obtained:

$$\begin{cases} I_T = I_F + I_m \\ E_0 = I_T Z_T + I_F Z_F \\ E_m = -I_m Z_m + I_F Z_F \end{cases} \quad (1)$$

By solving system of equations (1) expressions for the currents $I_m$, $I_F$, and $I_T$ can be derived as follows:

$$I_m = -\frac{V_m}{Z_m} + \frac{Z_F}{Z_m} \cdot \frac{V_F + V_m \frac{Z_T}{Z_m}}{Z_T + Z_F + \frac{Z_F Z_T}{Z_m}}, \quad (2)$$

$$I_F = \frac{V_T + V_m \cdot \frac{Z_T}{Z_m}}{Z_T + Z_F + \frac{Z_F Z_T}{Z_m}}, \text{ and} \quad (3)$$

$$I_T = \left(1 + \frac{Z_F}{Z_m}\right) \frac{V_T + V_m \cdot \frac{Z_T}{Z_m}}{Z_T + Z_F + \frac{Z_F Z_T}{Z_m}} - \frac{V_m}{Z_m} \cdot \frac{Z_F}{Z_m} \quad (4)$$

From equation (2), a optimal value of the voltage $V_m$, which corresponds to the condition of zero leakage (e.g., $I_m = 0$) can be derived:

$$V_m = V_T \frac{Z_F}{Z_F + Z_T} = \frac{V_T}{1 + \frac{Z_T}{Z_F}} \quad (5)$$

As can be seen from equation (5), the biasing required to set $I_m=0$ does not depend on the mandrel impedance $Z_m$ and is defined by the ratio between transmitting element impedance $Z_T$ and the measuring electrode impedance $Z_F$. Assuming that standoff is constant between the locations of the transmitting element 36 and the measurement electrode 38 and the formation 13 is homogenous, the ratio of $Z_T$ to $Z_F$ can be reduced to a ratio of the area of the transmitting element 36 to the area of the measurement electrode 38. In one case, Vm is equal to any value between 0.8 and 0.85 times $V_T$.

Referring again to FIG. 2, the imaging instrument 10 also includes a voltage biasing element 31. The biasing element 31 can provide $E_m$ at a level as described above between the mandrel 31 and a neutral 33 (e.g., ground). In one embodiment, the $E_0$ and $E_m$ have a common neutral.

Figure 5:
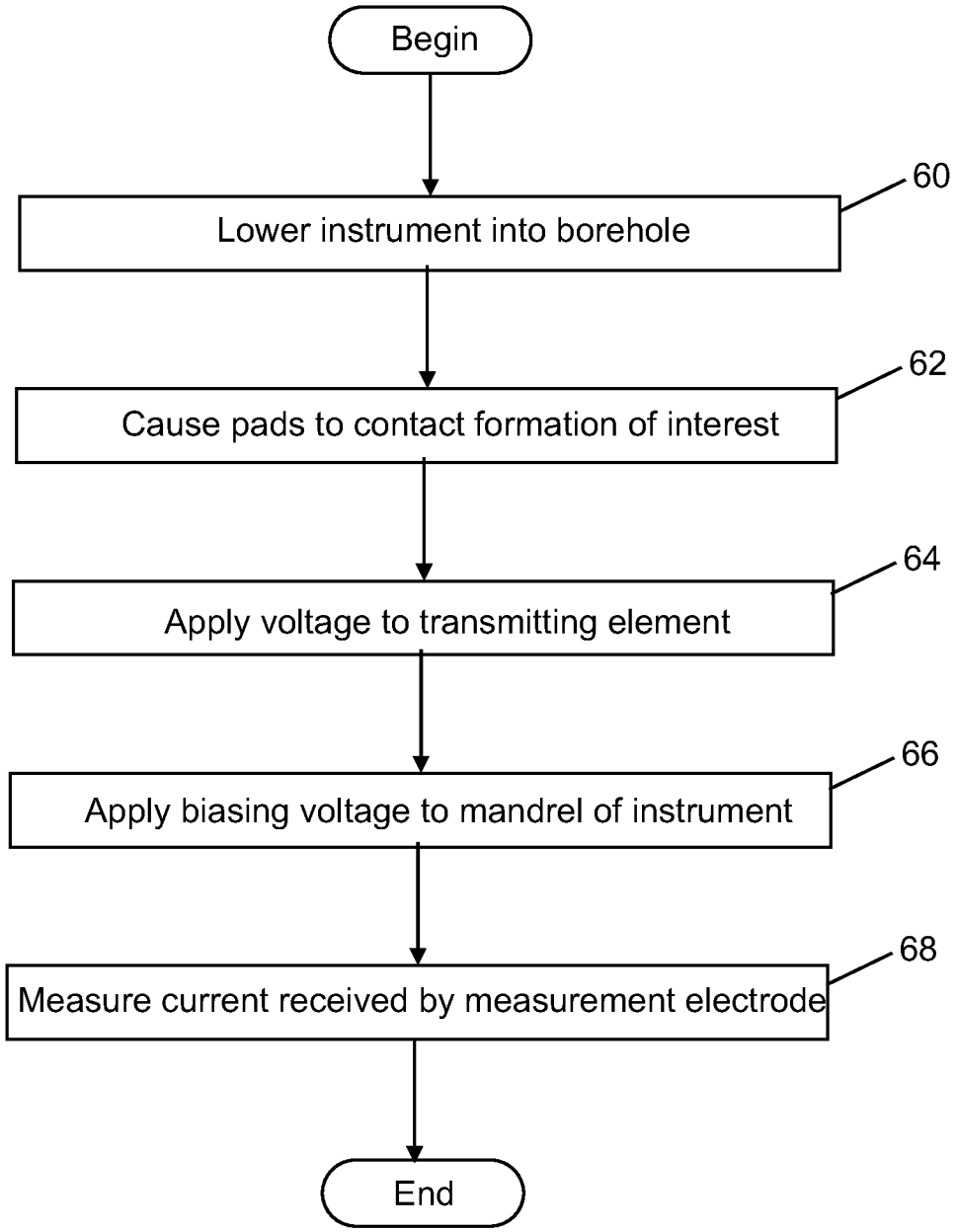
FIG. 5 is a flow chart illustrating a method of operating an imaging instrument according to one embodiment.

FIG. 5 illustrates a method of operating an imaging instrument such as, for example, imaging instrument 10 of FIG. 2. At block 60 the imaging instrument is lowered into a borehole and, at block 62, one or more pads carried by the instrument are caused to contact a formation of interest. At block 64 a voltage is applied to a transmitting element carried by one of the pads. During at least a portion of the time that the voltage is applied in block 64, a biasing voltage is applied to the mandrel of the imaging instrument as indicated at block 66. It shall be understood that the biasing voltage applied at block 66 can be determined in a manner the same or similar to that described above. At block 68 a current received by a measurement electrode on the pad is measured. In one embodiment, the measurement of current at block 68 occurs while the biasing voltage is applied to the mandrel.

The above description provides an exemplary system and method for reducing the effects of mandrel leakage by biasing the mandrel. In that embodiment, only a measurement of $I_F$ is required. In another embodiment, the above-described mandrel biasing can be combined with a correction for residual mandrel leakage. Such an embodiment includes also measuring the current $I_T$. Such a method, generally, includes taking note that the second equation of equation system (1) above, provides an estimate of $Z_f$ as defined in equation (6):

$$Z_f = \frac{E_0}{I_f + \alpha I_T} \quad (6)$$

where $\alpha$ is the ratio between the size of the measurement electrode 38 and the transmitting element 36, and a $Z_F$ is approximately equal to $Z_T$. It is further assumed that the real part of $Z_F$ is approximately equal to the resistance of the formation ($R_F$). In this embodiment, measuring $I_T$ allows for the derivation of the real part of the impedance of the measurement electrode 38 (FIG. 2). Such a derivation is, of course, independent of the mandrel and the transmitter as the impact of those elements is incorporated into the measurements of $I_T$ and $I_F$.

Both of the approaches described above are based on the assumption that the ratio between the impedances $Z_T$ and $Z_F$ is known in advance. Of course, in some instances, this ratio may uncontrollably vary due to either uneven standoff between the transmitting element and the button or due to non-homogeneity of a formation. Further, it may be difficult to maintain an optimal value of the biasing voltage $E_m$ (by magnitude and phase).

One approach to overcoming these issues can include making the measurements of the transmitter and button currents $I_T$, $I_F$ for two different values $E_m^{(1)}$, $E_m^{(2)}$ of the biasing voltages (hereafter the superscript denotes a number of the measurement mode). From the equivalent circuit shown in FIG. 4, the relationships in the system of equations (7) below can be derived.

$$Z_T I_T^{(1)} + Z_F I_F^{(1)} = E_0,$$

$$Z_T I_T^{(2)} + Z_F I_F^{(2)} = E_0, \quad (7)$$

From these two equations a formation impedance that is independent of $E_m^{(1)}$ and $E_m^{(2)}$ can be derived as shown in equation 8:

$$Z_F = \frac{E_0(I_T^{(1)} - I_T^{(2)})}{I_F^{(2)} I_T^{(1)} - I_F^{(1)} I_T^{(2)}} \quad (8)$$

Because the relationships in system 7 and equation 8 are independent of $E_m^{(1)}$ and $E_m^{(2)}$ there is no need to control the magnitude or phase of them. Of course, these two measurements should be linearly independent, for practical resolvability of system (7). In addition, because equation 8 is independent of $Re(Z_T)$, more flexibility in designing the transmitter can be realized.

Figure 6:
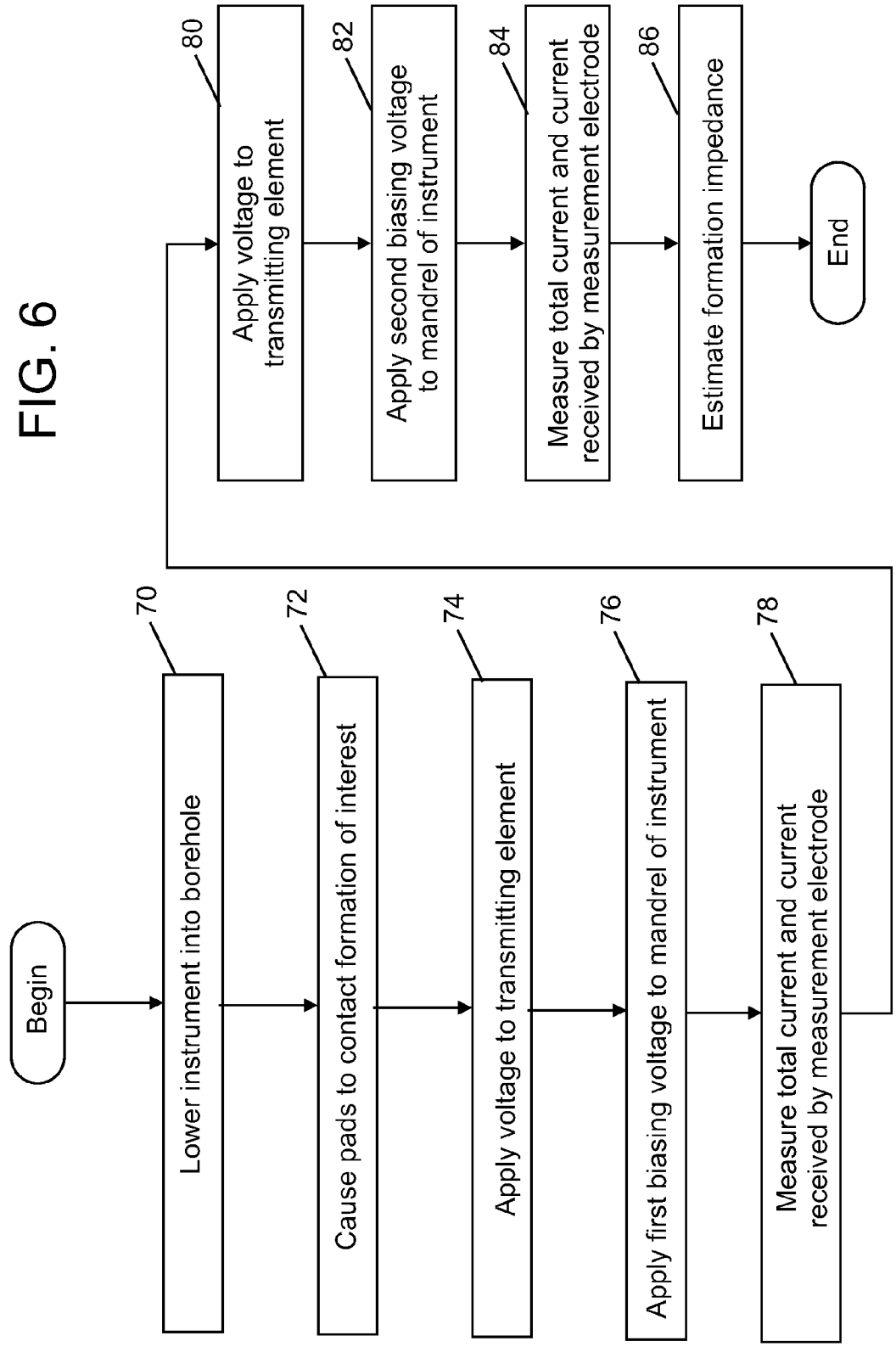
FIG. 6 is a flow chart illustrating a method of operating an imaging instrument according to another embodiment.

FIG. 6 is a flow chart illustrating a method of estimating the impedance of the formation ($Z_F$) according to one embodiment. In this embodiment, at block 70 the imaging instrument is lowered into a borehole and, at block 72, one or more pads carried by the instrument are caused to contact a formation of interest. At block 74 a voltage is applied to a transmitting element carried by one of the pads. During at least a portion of the time that the voltage is applied in block 74, a first biasing voltage is applied to the mandrel of the imaging instrument as indicated at block 76. At block 78 the formation current and the total current are measured during at least a portion of the time that the first biasing voltage is applied. These values are represented as $I_F^{(1)}$ and $I_T^{(1)}$, respectively, in equation 8 above. Following block 76, at block 80 a voltage is again applied to the transmitting element carried by one of the pads. During at least a portion of the time that the voltage is applied in block 80, a second biasing voltage is applied to the mandrel of the imaging instrument as indicated at block 82. At block 84 the formation current and the total current are measured during at least a portion of the time that second biasing voltage is applied. These values are represented as $I_F^{(2)}$ and $I_T^{(2)}$, respectively, in equation 8 above. At block 86 and estimate of $Z_F$ can be formed from the values collected in blocks 78 and 84. It will be understood that a time delay may exist between blocks 76 and 80 and the voltage applied to the pad can be terminated during the delay to ensure lineal independence of the measurements made in block 78 and 84. Further, it shall be understood that while the term impedance has been used for the description above, one of ordinary skill will realize that resistivity estimates could also be made if the time varying components of the measured signal is filtered out or otherwise ignored.

Elements of the embodiments have been introduced with either the articles "a" or "an." The articles are intended to mean that there are one or more of the elements. The terms "including" and "having" are intended to be inclusive such that there may be additional elements other than the elements listed. The conjunction "or" when used with a list of at least two terms is intended to mean any term or combination of terms. The terms "first," "second," and "third" are used to distinguish elements and are not used to denote a particular order.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of estimating a parameter of a formation contacting a borehole with an instrument that includes a mandrel and a pad, the method comprising:
   providing a measurement voltage to the pad;
   applying a biasing voltage to the mandrel while the measurement voltage is applied to the pad;
   measuring a received current during at least a portion of time the measurement voltage is provided; and
   estimating the parameter based on the received current.

2. The method of claim 1, further comprising:
   lowering the instrument into the borehole; and
   causing the pad to contact the formation.

3. The method of claim 1, wherein the biasing voltage is lower than the measurement voltage.

4. The method of claim 3, wherein the biasing voltage is between 0.8 and 0.85 times the measurement voltage.

5. The method of claim 1, wherein the measurement voltage and the biasing voltage are alternating current (AC) voltages.

6. The method of claim 1, wherein the parameter is resistivity.

7. The method of claim 1, wherein the parameter is impedance.

8. The method of claim 1, wherein the measurement voltage is applied to a transmitting element in the pad and the received current is received by a measurement electrode.

9. The method of claim 1, wherein the transmitting element is a metal plate and the measurement electrode is located in the pad.

10. A method of estimating a parameter of a formation contacting a borehole with an instrument that includes a mandrel and a pad, the method comprising:
    providing a measurement voltage to the pad;
    applying a first biasing voltage to the mandrel while the measurement voltage is applied to the pad;
    measuring a first total current provided to the pad while the first biasing voltage is applied;
    measuring a first received current while the first biasing voltage is provided;
    applying a second biasing voltage to the mandrel while the measurement voltage is applied to the pad and after the first biasing voltage is applied;
    measuring a second received current while the second biasing voltage is provided;
    measuring a second total current applied provided to the pad while the second biasing voltage is applied; and
    estimating the parameter based on the first and second received currents and the first and second total currents.

11. The method of claim 10, wherein the parameter is impedance.

12. The method of claim 11, wherein the impedance is estimated based on the relationship:

$$Z_F = \frac{E_0(I_T^{(1)} - I_T^{(2)})}{I_F^{(2)} I_T^{(1)} - I_F^{(1)} I_T^{(2)}}$$

where $Z_F$ is the impedance, $E_0$ is the measurement voltage, $I_T^{(1)}$ is the first total current, $I_T^{(2)}$ is the second total current, $I_F^{(1)}$ is the first received current and $I_F^{(2)}$ is the second received current.

13. The method of claim 10, further comprising:
    lowering the instrument into the borehole; and
    causing the pad to contact the formation.

14. The method of claim 10, wherein the first voltage and the first and second biasing voltages are alternating current (AC) voltages.

15. A measurement instrument for measuring a parameter of formation contacting a borehole, the measurement instrument comprising:
    a mandrel;
    a pad that carries a transmitting element and a measurement electrode, the pad being coupled to the mandrel such that it can be extended outwardly away from the mandrel to contact the formation;
    a measurement voltage provider that provides a measurement voltage to the transmitting element; and
    a biasing voltage provider that provides a biasing voltage to the mandrel at least a portion of the time the measurement voltage is provided.

16. The measurement instrument of claim 15, further comprising:
    a current meter configured to measure the current provided to the transmitting element while the measurement voltage is provided.

* * * * *